(12) United States Patent
Finn et al.

(10) Patent No.: US 11,272,850 B2
(45) Date of Patent: Mar. 15, 2022

(54) CATHETER AND METHOD FOR CALCULATING FRACTIONAL FLOW RESERVE

(71) Applicant: Medtronic Vascular, Inc., Santa Rosa, CA (US)

(72) Inventors: Ronan Finn, County Galway (IE); John Kelly, Galway (IE); Matthew Fleming, Roscommon (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 758 days.

(21) Appl. No.: 15/671,686

(22) Filed: Aug. 8, 2017

(65) Prior Publication Data
US 2018/0042492 A1   Feb. 15, 2018

Related U.S. Application Data

(60) Provisional application No. 62/372,349, filed on Aug. 9, 2016.

(51) Int. Cl.
*A61B 5/0215* (2006.01)
*A61B 5/00* (2006.01)
*A61B 5/026* (2006.01)
*A61B 5/02* (2006.01)

(52) U.S. Cl.
CPC ............ *A61B 5/0215* (2013.01); *A61B 5/026* (2013.01); *A61B 5/02007* (2013.01); *A61B 5/6852* (2013.01); *A61B 2562/0247* (2013.01)

(58) Field of Classification Search
CPC ....................................... A61B 5/0215–02158
See application file for complete search history.

(56) References Cited

U.S. PATENT DOCUMENTS

| | | | |
|---|---|---|---|
| 4,718,425 A | 1/1988 | Tanaka et al. | |
| 4,771,782 A | 9/1988 | Millar | |
| 4,796,641 A | 1/1989 | Mills et al. | |
| 4,815,472 A | 3/1989 | Wise et al. | |
| 4,850,358 A | 7/1989 | Millar | |
| 4,901,731 A | 2/1990 | Millar | |
| 4,924,877 A | 5/1990 | Brooks | |

(Continued)

FOREIGN PATENT DOCUMENTS

| CN | 101983031 A | 3/2011 |
|---|---|---|
| DE | 102008045878 | 3/2010 |

(Continued)

OTHER PUBLICATIONS

Office Action dated Apr. 2, 2020, in Chinese Application No. 201580032242.1 (with English Translation).

*Primary Examiner* — Meredith Weare
(74) *Attorney, Agent, or Firm* — Medler Ferro Woodhouse & Mills PLLC

(57) ABSTRACT

A catheter for measuring a fractional flow reserve includes a proximal shaft, a distal shaft coupled to a distal portion of the proximal shaft, and a pressure sensor coupled to the distal shaft. The distal shaft includes a middle wall portion configured to extend through a stenosis in a vessel. The middle wall portion of the distal shaft includes at least one skive reducing the cross-sectional profile of the middle wall portion. The middle wall portion may further include at least one stiffening wire for increasing columnar stiffness of the middle wall portion.

18 Claims, 13 Drawing Sheets

(56) References Cited

U.S. PATENT DOCUMENTS

| | | |
|---|---|---|
| 4,928,693 A | 5/1990 | Goodin et al. |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A | 7/1991 | Lieber et al. |
| 5,046,497 A * | 9/1991 | Millar ............... A61B 5/14539 600/309 |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Corl et al. |
| 5,813,997 A | 9/1998 | Imran et al. |
| 5,827,243 A | 10/1998 | Palestrant |
| 5,873,835 A | 2/1999 | Hastings et al. |
| 5,902,248 A | 5/1999 | Millar et al. |
| 5,964,714 A | 10/1999 | Lafontaine |
| 6,033,366 A | 3/2000 | Brockway et al. |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,179,856 B1 | 1/2001 | Barbere |
| 6,182,513 B1 | 2/2001 | Stemme et al. |
| 6,193,669 B1 | 2/2001 | Degany et al. |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 11/2001 | Hoek et al. |
| 6,336,906 B1 | 1/2002 | Hammarstrom et al. |
| 6,354,999 B1 | 3/2002 | Dgany et al. |
| 6,379,308 B1 | 4/2002 | Brockway et al. |
| 6,394,986 B1 | 5/2002 | Millar |
| 6,409,677 B1 | 6/2002 | Tulkki |
| 6,413,228 B1 * | 7/2002 | Hung ............... A61B 10/0045 600/562 |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 | 5/2004 | Atsumi |
| 6,754,608 B2 | 6/2004 | Svanerudh et al. |
| 6,767,327 B1 | 7/2004 | Corl et al. |
| 6,821,287 B1 | 11/2004 | Jang |
| 6,860,851 B2 | 3/2005 | Knudson |
| 6,868,736 B2 | 3/2005 | Sawatari et al. |
| 6,926,674 B2 | 8/2005 | Tenerz et al. |
| 6,938,474 B2 | 9/2005 | Melvangs |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway et al. |
| 7,060,038 B2 | 6/2006 | Letort et al. |
| 7,097,620 B2 | 8/2006 | Corl et al. |
| 7,112,170 B2 | 9/2006 | Schock et al. |
| 7,134,994 B2 | 11/2006 | Alpert et al. |
| 7,137,953 B2 | 11/2006 | Eigler et al. |
| 7,211,048 B1 | 5/2007 | Najafi et al. |
| 7,222,539 B2 | 5/2007 | Tulkki |
| 7,229,403 B2 | 6/2007 | Schock et al. |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B2 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway et al. |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson et al. |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson et al. |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,696,584 B2 | 4/2014 | Kassab |
| 8,698,638 B2 | 4/2014 | Samuelsson et al. |

(56) References Cited

U.S. PATENT DOCUMENTS

| | | |
|---|---|---|
| 8,714,021 B2 | 5/2014 | Gamage |
| 8,797,155 B2 | 8/2014 | Huennekens et al. |
| 8,857,264 B2 | 10/2014 | Gamage |
| 8,860,851 B2 | 10/2014 | Goma et al. |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0144623 A1* | 7/2003 | Heath et al. .......... A61M 25/00 604/4.01 |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan et al. |
| 2005/0222532 A1* | 10/2005 | Bertolero ............ A61M 1/3659 604/4.01 |
| 2005/0267408 A1* | 12/2005 | Grandt et al. .... A61M 25/0021 604/103.04 |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith et al. |
| 2008/0077085 A1 | 3/2008 | Eidenschink et al. |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Naghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0247947 A1* | 10/2009 | Pepper ................ A61M 25/10 604/103.04 |
| 2009/0248049 A1 | 10/2009 | Perkins |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0109104 A1 | 5/2010 | Tlensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1* | 9/2010 | Manstrom ............ A61M 5/007 600/301 |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0046522 A1* | 2/2011 | Chan ................ A61B 17/22012 601/2 |
| 2011/0060229 A1 | 3/2011 | Hulvershorn et al. |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1* | 7/2012 | Smith ................ A61B 5/0215 600/486 |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |

(56) References Cited

U.S. PATENT DOCUMENTS

| | | |
|---|---|---|
| 2013/0131523 A1* | 5/2013 | Suchecki ............ A61B 5/6851 600/486 |
| 2013/0190633 A1 | 7/2013 | Dorando et al. |
| 2013/0216481 A1 | 8/2013 | Rosenmeier |
| 2013/0303914 A1 | 11/2013 | Hiltner et al. |
| 2013/0324864 A1 | 12/2013 | Manstrom et al. |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0180141 A1 | 6/2014 | Millett |
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0073336 A1* | 3/2015 | Moehle ............ A61M 25/003 604/35 |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173629 A1* | 6/2015 | Corl et al. ............ A61B 5/0215 600/424 |
| 2015/0173722 A1 | 6/2015 | Huennekens et al. |
| 2015/0196210 A1* | 7/2015 | McCaffrey ........ A61B 5/02158 600/488 |
| 2015/0223707 A1 | 8/2015 | Ludoph |
| 2015/0265167 A1 | 9/2015 | McGowan et al. |
| 2015/0272449 A1* | 10/2015 | Meyer ................ A61B 5/0215 600/424 |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0066802 A1 | 3/2016 | Keller |
| 2016/0106321 A1 | 4/2016 | Sharma et al. |
| 2017/0189654 A1* | 7/2017 | Schwartz ........... A61M 25/1011 |

FOREIGN PATENT DOCUMENTS

| | | |
|---|---|---|
| EP | 0263190 | 10/1986 |
| EP | 1658808 | 8/1995 |
| EP | 1260175 | 11/2002 |
| EP | 1419796 | 5/2004 |
| EP | 1493381 | 1/2005 |
| EP | 1514512 | 3/2005 |
| EP | 1702641 | 9/2006 |
| JP | 10033488 | 10/1998 |
| JP | 2000333913 | 12/2000 |
| JP | 2004-194996 | 7/2004 |
| JP | 2005095603 | 4/2005 |
| JP | 20053638066 | 4/2005 |
| JP | 20053705458 | 10/2005 |
| JP | 2006204378 | 8/2006 |
| JP | 10137199 | 5/2010 |
| NL | 2009285 | 8/2012 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/0117154 | 11/2006 |
| WO | WO2011/0120565 | 10/2011 |
| WO | WO2011/0161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

* cited by examiner

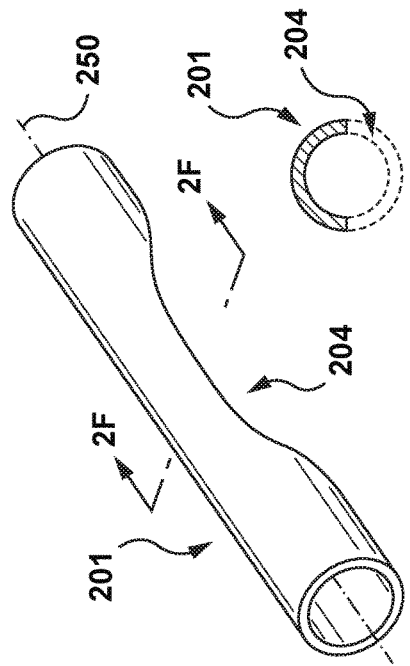
FIG. 2E
FIG. 2F
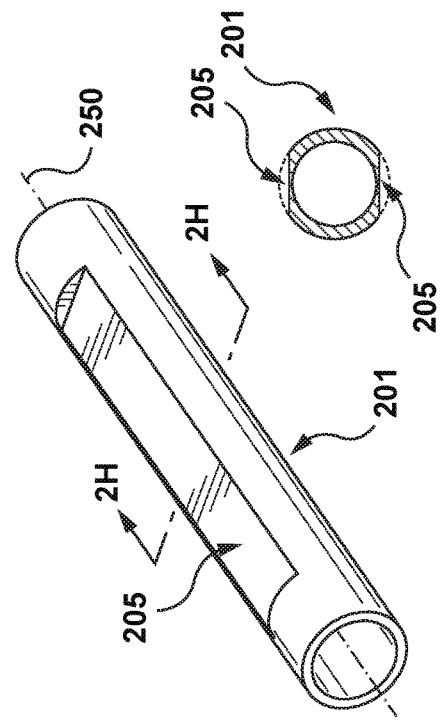
FIG. 2G
FIG. 2H
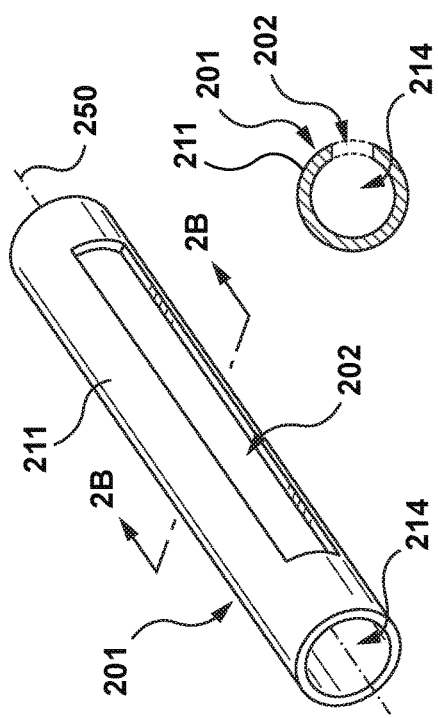
FIG. 2A
FIG. 2B
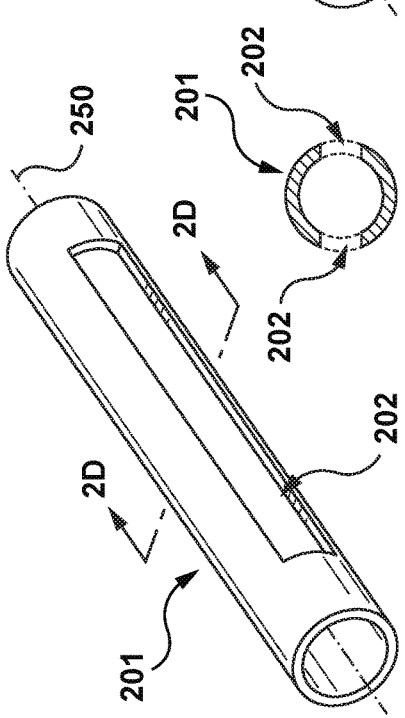
FIG. 2C
FIG. 2D

BACKGROUND

BACKGROUND

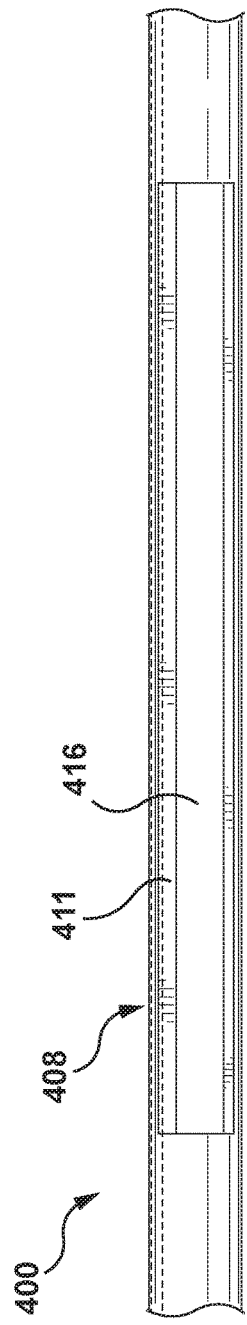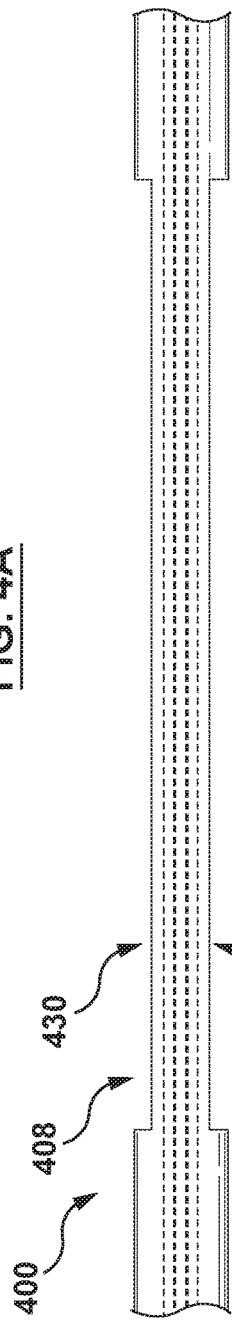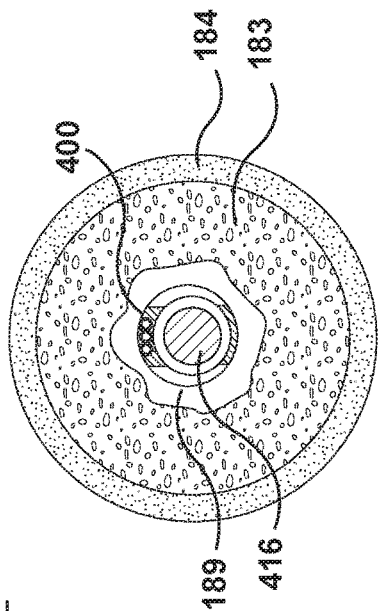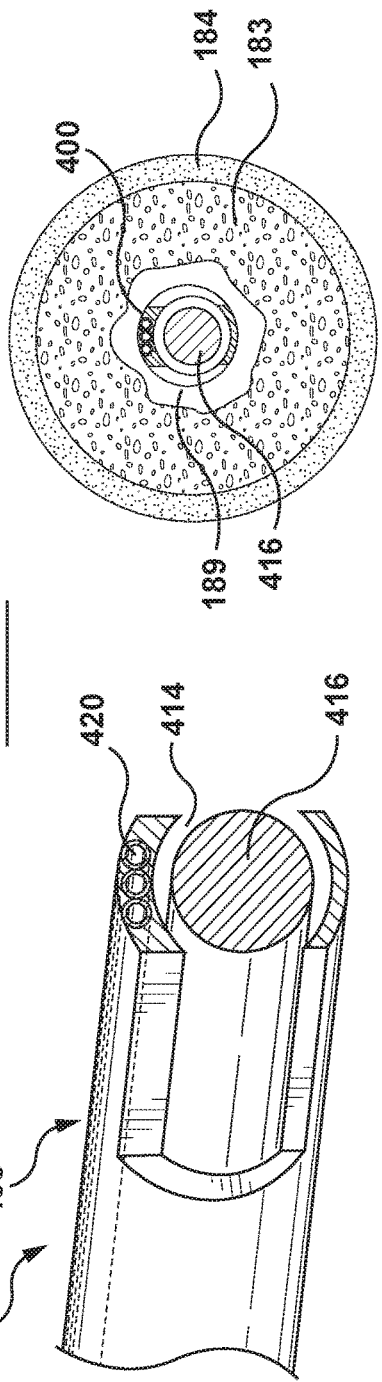

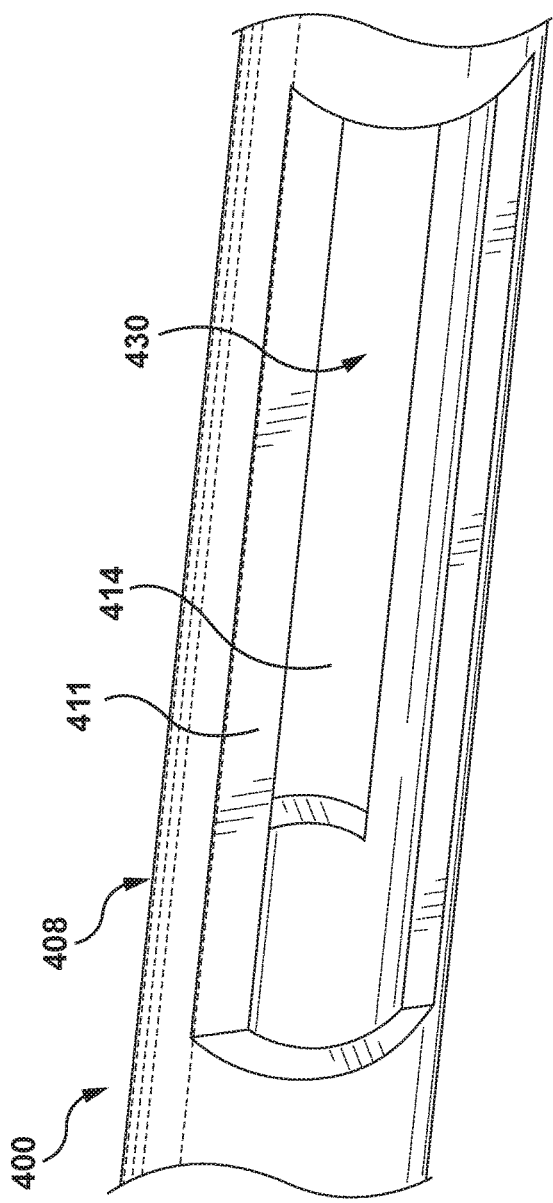
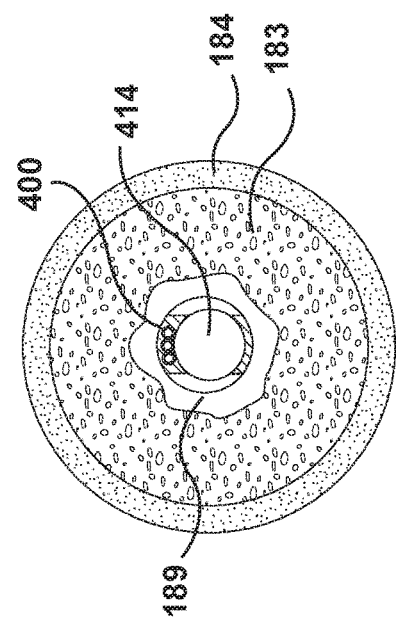
FIG. 5A
FIG. 5B

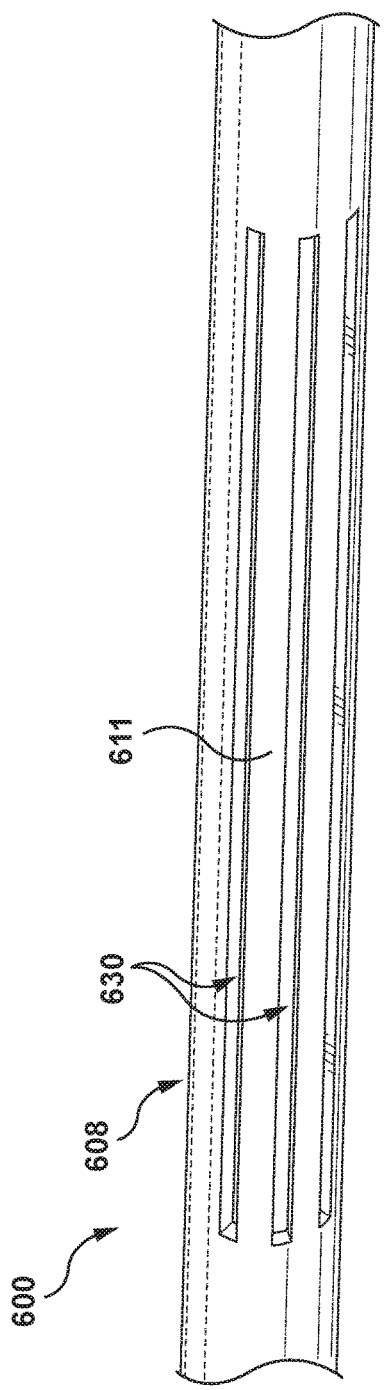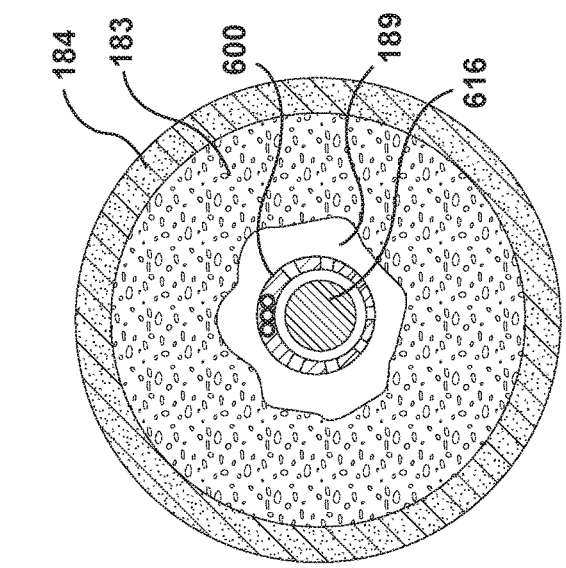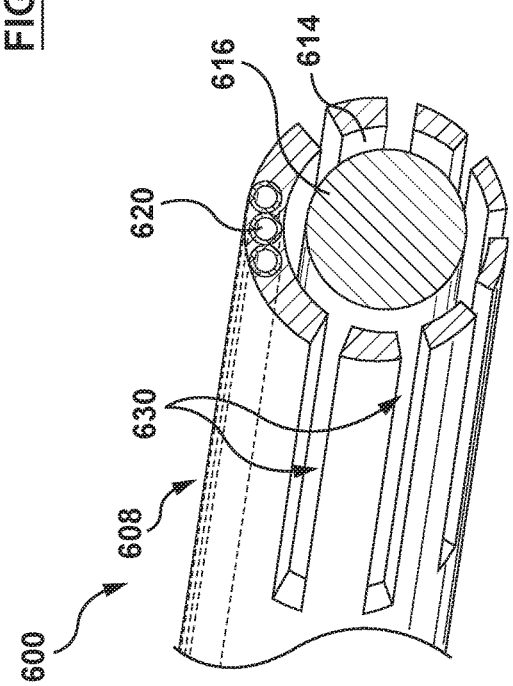

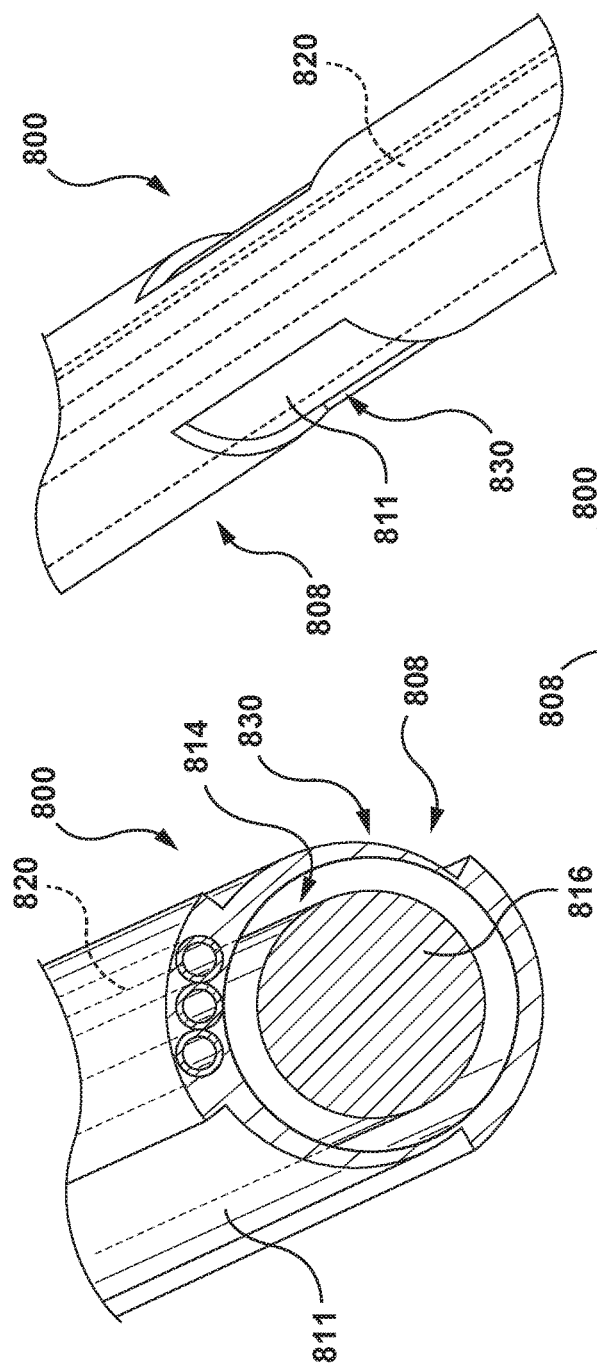
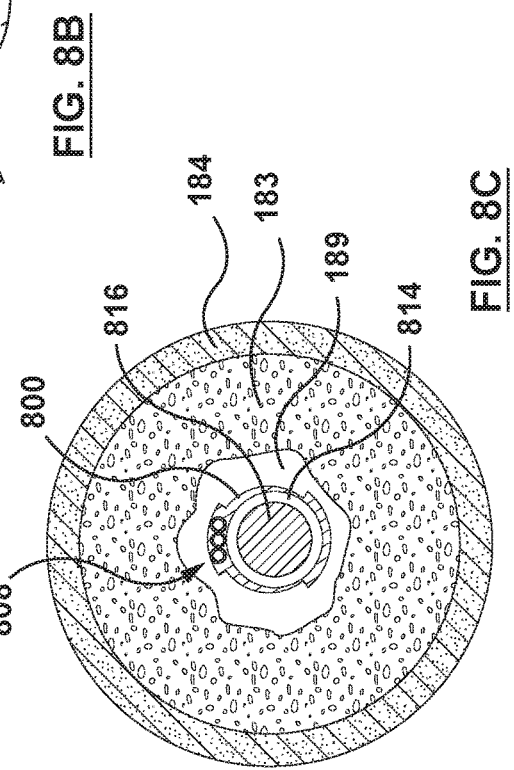
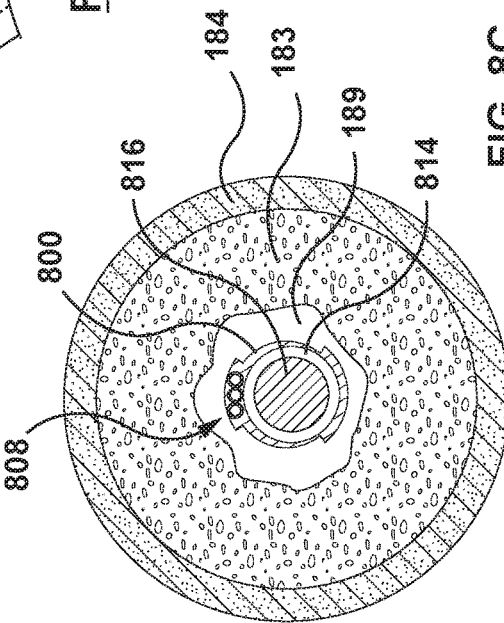

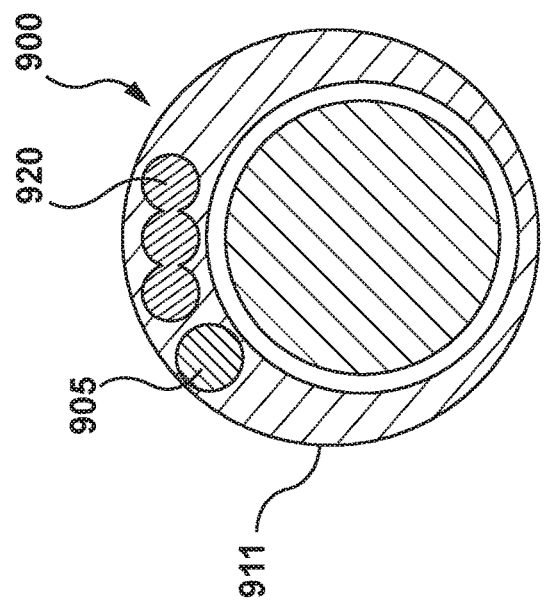
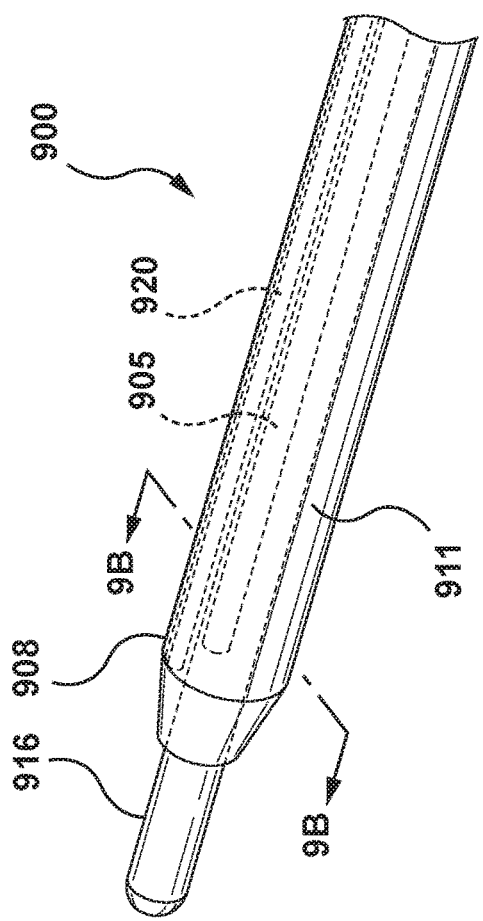
FIG. 9B
FIG. 9A

CATHETER AND METHOD FOR CALCULATING FRACTIONAL FLOW RESERVE

CROSS-REFERENCE TO RELATED APPLICATIONS

This application claims the benefit under 35 U.S.C. § 119(e) of the filing date of U.S. Provisional Patent Application No. 62/372,349, filed Aug. 9, 2016, which is incorporated by reference herein in its entirety.

FIELD OF THE INVENTION

The present invention relates to systems and methods for determining a Fractional Flow Reserve. More particularly, the present invention relates to a catheter configured for reduced interference with a Fractional Flow Reserve measurement.

BACKGROUND OF THE INVENTION

The severity of a stenosis or lesion in a blood vessel may be assessed by obtaining proximal and distal pressure measurements relative to the given stenosis and using those measurements for calculating a value of a Fractional Flow Reserve (FFR). FFR is defined as the ratio of a distal pressure $P_d$ measured on a distal side of a stenosis to a proximal pressure $P_a$ measured on a proximal side of the stenosis, typically within the aorta (FFR=$P_d/P_a$). Conventionally, a sensor is placed on a distal portion of a guidewire (FFR wire) to obtain/measure the distal pressure $P_d$, while an external pressure transducer is fluidly connected via tubing to a guide catheter for obtaining the proximal, or aortic (AO) pressure $P_a$. Once the guide catheter is positioned in situ, and the pressure of the blood filling the lumen of the guide catheter is equal to the pressure of the blood at the distal tip of the guide catheter, tubing that fluidly connects the proximal end of the guide catheter to the external pressure transducer also fills with blood such that the external pressure transducer measures the pressure of the blood at the distal tip of the guide catheter. The FFR wire is advanced through the guide catheter and through the stenosis to a distal side of the stenosis. The sensor on the FFR wire measures the distal pressure.

Calculation of the FFR value provides a stenosis specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation. If an interventional treatment is required, the interventional device, such as a balloon catheter, is tracked over a guidewire to the site of the stenosis. Conventional FFR wires generally are not desired by clinicians to be used as guidewires for such interventional devices. Accordingly, if an interventional treatment is required, the clinician generally removes the FFR wire, inserts a conventional guidewire, and tracks the interventional device to the treatment site over the conventional guidewire.

To address this concern, efforts have been made to utilize catheters to take pressure measurements for calculating FFR. Using a catheter (FFR catheter or micro-catheter), a clinician may use a preferred guidewire for tracking the FFR catheter to the site of the stenosis. If an interventional treatment is required, the FFR catheter may be removed while the guidewire used with the FFR catheter may remain in situ, and the interventional device may be tracked over the existing guidewire to the site of the stenosis.

However, such FFR catheters are generally larger in cross-sectional profile than FFR wires, which are typically 0.014" in diameter. Therefore, some deviation may be introduced into the measured proximal pressure $P_a$ and the measured distal pressure $P_d$, as compared to measurements taken using an FFR wire. In particular, the larger cross-sectional profile of a distal portion of an FFR catheter, as compared to an FFR wire, occupies a larger percentage of the vessel distal of the guide catheter and across the stenosis. Occupying a larger percentage of the intra-stenosis lumen affects the fluid dynamics of the blood flow through the stenosis, thereby causing the measured distal pressure $P_d$ to deviate from distal pressure of the same vessel and same stenosis measured with a conventional FFR wire. Deviation of the measured distal pressure $P_d$ is transferred to the calculated FFR.

Thus, using an FFR catheter may cause the calculated FFR to deviate from FFR calculated using measurements taken with an FFR wire. Because interventional decisions have been made based on FFR measured using FFR wires, this can lead to "false positives." A "false positive" is where the FFR calculated using measurements taken with an FFR catheter is lower than the threshold for intervention (e.g. below 0.80) but if the FFR were calculated using measurements taken with an FFR wire, the FFR would have been higher than the threshold (e.g. above 0.80).

Accordingly, there is a need to reduce the cross-sectional profile of FFR catheters to minimize deviation of FFR calculated using an FFR catheter as compared to FFR calculated using an FFR guidewire.

BRIEF SUMMARY OF THE INVENTION

Embodiments described herein relate to a catheter for measuring a fractional flow reserve. The catheter includes a proximal shaft, a distal shaft, a pressure sensor, and at least one pressure sensor wire. In embodiments, the distal shaft of the catheter includes one or more skives reducing the cross-sectional profile of the catheter in a portion configured to extend through an arterial stenosis.

In an embodiment, a catheter for measuring a fractional flow reserve includes a proximal shaft, a distal shaft, and a pressure sensor coupled to the distal shaft. The distal shaft includes a proximal wall portion, a middle wall portion, and a distal wall portion. The distal shaft defines a guidewire lumen configured to receive a guidewire therein. At least one skive is disposed in the middle wall portion configured to reduce a cross sectional profile of the middle wall portion.

In another embodiment, a method for calculating a Fractional Flow Reserve in a vessel using a catheter includes delivering a distal shaft of the catheter to a treatment site in the vessel. The distal shaft defines a guidewire lumen and includes a distal wall portion, a middle wall portion, and a proximal wall portion. The middle wall portion includes at least one skive reducing a cross sectional profile of the distal shaft at the middle wall portion. The catheter includes a pressure sensor coupled to the distal wall portion of the catheter. The catheter is delivered to the treatment site such that the distal wall portion is disposed on a distal side of a stenosis of the vessel, the skive of middle wall portion is disposed through an intra-stenosis lumen of the stenosis, and the proximal wall portion is disposed on a proximal side of the stenosis of the vessel. The method further includes measuring a pressure distal of the stenosis using the pressure sensor, measuring a pressure proximal of the stenosis, and calculating the Fractional Flow Reserve using the measured distal pressure and the measured proximal pressure.

BRIEF DESCRIPTION OF DRAWINGS

FIGS. 2A-2H illustrate examples of skives in catheter walls, consistent with embodiments described herein.

FIGS. 4A-4D illustrate different views of a catheter with dual skives, consistent with embodiments described herein.

FIGS. 5A-5B illustrate a catheter with dual skives having a withdrawn guidewire, consistent with embodiments described herein.

FIGS. 6A-6C illustrate a catheter with multiple skives, consistent with embodiments described herein.

FIGS. 8A-8C illustrates a catheter having a non-penetrating skive, consistent with embodiments described herein.

FIGS. 9A-9B illustrate a catheter having a circular stiffening wire, consistent with embodiments described herein.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a vessel or a stenosis are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful, such as, but not limited to peripheral arteries, carotid arteries, renal arteries, and/or venous applications. Furthermore, there is no intention to be bound by any expressed or implied theory presented in the preceding technical field, background, brief summary, or the following detailed description.

Figure 1:
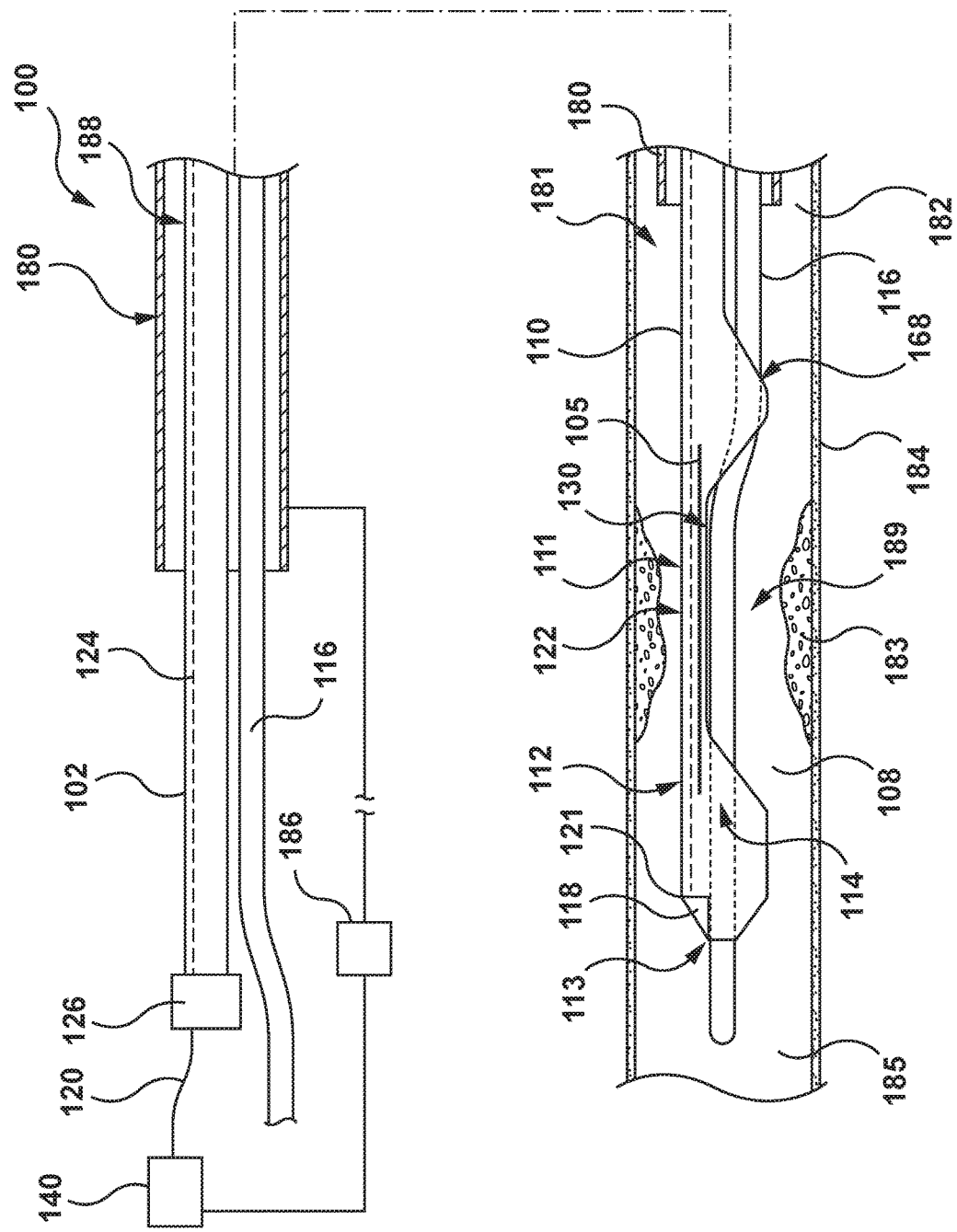
FIG. 1 is a side illustration of a catheter for calculating a Fractional Flow Reserve (FFR) in accordance with an embodiment hereof.

FIG. 1 illustrates a catheter 100 for calculating a Fractional Flow Reserve (FFR) according to an embodiment of the present disclosure. The catheter 100 includes a proximal shaft 102, a distal shaft 108, a pressure sensor 118, and at least one pressure sensor wire 120. The catheter 100 includes a hub or handle 126 coupled to a proximal end of the proximal shaft 102 for convenient handling of the catheter 100, as shown in FIG. 1. The catheter 100 is configured to be disposed in a vessel 184 with a proximal portion of the proximal shaft 102 extending outside of a patient, and a distal portion of the distal shaft 108 positioned in situ within a lumen 181 of the vessel 184 having a lesion or stenosis 183. The catheter 100 is configured to measure a distal pressure $P_d$ on a distal side 185 of the stenosis 183. Various features of the components of the catheter 100 reflected in FIG. 1 and described below may be modified or replaced with different structures and/or mechanisms.

The proximal shaft 102 may be formed of, for example, and not by way of limitation, polyether block amide (e.g., VESTAMID or PEBAX), thermoplastic elastomers (TPE), or other materials suitable for the purposes described herein. The proximal shaft 102 is coupled to the hub/handle 126 by, for example, and not by way of limitation, adhesives, mechanical connection, fusing, welding, for any other method suitable for the purposes of the present disclosure. As illustrated in FIG. 1, proximal shaft 102 of catheter 100 is configured to run alongside of the guidewire 116 within a guide catheter 180. Consistent with the present disclosure, the proximal shaft 102 may also be provided in various alternatives. The proximal shaft 102 may be solid or may include one or more lumens. In some embodiments, the proximal shaft 102 may be or may include a wire. The proximal shaft 102 is configured for pushing distal shaft 108 through the guide catheter 180 and for housing or otherwise containing sensor wires 120. Any variations of the proximal shaft 102 that permit these functions to be fulfilled are within the scope of this disclosure.

FIG. 1 also illustrates an embodiment of the distal shaft 108 of the catheter 100. The distal shaft 108 includes a distal shaft wall 122, including a proximal wall portion 110, a middle wall portion 111, and a distal wall portion 112. The distal shaft 108 defines a guidewire lumen 114 extending from the proximal wall portion 110 to the distal wall portion 112. The distal shaft 108 further includes the pressure sensor 118 and a distal portion of the pressure sensor wire 120. The distal shaft 108 is configured to extend from a proximal side 182 of the stenosis 183, through an intra-stenosis lumen 189, to the distal side 185 of the stenosis 183 such that the pressure sensor 118 is disposed on the distal side 185 of the stenosis 183, as shown in FIG. 1. The intra-stenosis lumen 189 is the lumen extending through the stenosis 183, and has a reduced area or profile as compared to the blood vessel 184 due to the existence of the stenosis 183. The guidewire lumen 114 is configured to receive a guidewire 116 therein. A proximal guidewire port 168 is disposed at a proximal end of the distal shaft 108. A distal guidewire port 113 is disposed in the distal wall portion 112 of the distal shaft 108. The distal portion of the pressure sensor wire 120 is disposed within distal shaft wall 122 of the distal shaft 108. The distal shaft 108 may be formed of, for example, and not by way of limitation, polyethylene, polyether block amide (e.g., VESTAMID or PEBAX), polyamide and/or combinations thereof, either blended or co-extruded, or other materials suitable for the purposes described herein. The distal shaft 108 may be coupled to the proximal shaft 102 by, for example, and not by way of limitation, adhesives, fusing, welding, for any other method suitable for the purposes of the present disclosure. In other embodiments, the proximal shaft 102 and the distal shaft 108 may be formed unitarily.

The distal shaft 108 and proximal shaft 102 may be configured for rapid exchange. As illustrated in FIG. 1, the distal shaft 108 includes the guidewire lumen 114 for the guidewire 116, while the proximal shaft 102 runs next to the guidewire 116 within the guide catheter 180. This may permit a physician to insert and remove the catheter 100 over the guidewire 116 without requiring the out-of-vasculature portion of the guidewire 116 to extend the length of the catheter 100. In alternative embodiments, the distal shaft 108 and the proximal shaft 102 may be an over-the-wire design, with the guidewire lumen 114 extending into and through an entire length of proximal shaft 102.

The pressure sensor 118 of the distal shaft 108, as shown in FIG. 1, may be a piezo-resistive pressure sensor, a piezo-electric pressure sensor, a capacitive pressure sensor, an electromagnetic pressure sensor, an optical pressure sensor, and/or combinations thereof or other sensors suitable for the purposes described herein. The pressure sensor 118 is configured to measure a pressure of a fluid outside the distal shaft 108. With the pressure sensor 118 disposed on the distal side 185 of the stenosis 183, the pressure sensor 118 measures the distal pressure $P_d$ of a fluid (blood) outside of the distal shaft 108. The pressure sensor 118 is further configured to communicate the distal pressure $P_d$ to a processor 140. The pressure sensor 118 is coupled to the distal shaft 108 of the catheter 100 such that the pressure sensor 118 is disposed on the distal side 185 of the stenosis 183 when the distal shaft 108 is positioned at a treatment site therein, as shown in FIG. 1. The pressure sensor 118 may be coupled to the distal shaft 108 by, for example and not by way of limitation, adhesives, fusing, welding, for any other method suitable for the purposes of the present disclosure. Further, additional features may be provided as part of the distal shaft 108 for housing the pressure sensor 118, such as pockets, openings, and similar features.

The pressure sensor wire(s) 120 include a proximal end coupled to the processor 140 and a distal end 121 coupled to the pressure sensor 118. The pressure sensor wire(s) 120 are configured such that the pressure sensor 118 is in communication with the processor 140. The pressure sensor wire(s) 120 are disposed within a shaft wall 124 of the proximal shaft 102 and the distal shaft wall 122 of the distal shaft 108 such that the pressure sensor wire(s) 120 extend(s) proximally from the pressure sensor 118, through the distal shaft wall 122, through the proximal shaft wall 124, exiting through the hub/handle 126 to the processor 140. The pressure sensor wire(s) 120 may be coupled to the pressure sensor 118 by, for example, and not by way of limitation, adhesives, fusing, welding, or any other method suitable for the purposes of the present disclosure. The pressure sensor wire(s) 120 may be coupled to the processor 140 by, for example and not by way of limitation, cables, connectors, antennas, routers, switches, optical and/or fluid connections, wireless connections, and/or any other coupling suitable for the purposes described herein.

The pressure sensor wires 120 may include one or more pressure sensor wires, and illustrations herein including specific numbers of wires are not meant to limit the design, and more or fewer pressure sensor wires 120 may be utilized. In an embodiment, the pressure sensor wire(s) 120 is a tri-filar wire. Moreover, the pressure sensor wires 120 may be eliminated in embodiments wherein a signal from the pressure sensor 118 is sent to the processor 140 other than via the pressure sensor wires 120, such as, but not limited to, a wireless transmission.

The processor 140 may be any processor suitable for the purposes described herein. The processor 140 may include such components as a CPU, a display device, an amplification and filtering device, an analog-to-digital converter, and various other components. The processor 140 is configured to receive a measured proximal pressure $P_a$ and a measured distal pressure $P_d$, and to calculate FFR from the measured distal pressure $P_d$ and the measured proximal pressure $P_a$. The processor 140 may be further configured to provide a continuous display of calculated Fractional Flow Reserve (FFR). The processor 140 is coupled to the pressure sensor wires(s) 120 such that the processor 140 is in communication with the pressure sensor 118 as described previously. The processor 140 is coupled to a proximal end of the pressure sensor wire(s) 120 as described above. Accordingly, it is understood that additional components (e.g., cables, connectors, antennas, routers, switches, etc.) not illustrated in FIG. 1 may be included to facilitate communication between the proximal end of the pressure sensor wire(s) 120 and the processor 140. In other embodiments, instead of the pressure sensor wire(s) 120, communication between the pressure sensor 118 and the processor 140 may be accomplished wirelessly.

The distal shaft 108 further includes at least one skive 130, located in the middle wall portion 111 of the distal shaft 108. The skive 130, as illustrated in FIG. 1 and FIGS. 2A-2H, results in a reduced cross section through the middle wall portion 111 of the distal shaft 108, as compared to a shaft without a skive. In some embodiments, the skived middle wall portion 111 may be bounded by a fully intact circumferential distal wall portion 112 and a fully intact circumferential proximal wall portion 110, each having no skives 130. In some embodiments, the distal wall portion 112 and the proximal wall portion 110 may also include skives 130.

As used herein, a skive is a slot, cut, or other opening in a structure. Skiving a structure, e.g., creating a skive, may include shaving, ablating, paring, cutting, splitting, or other actions that remove material from the structure. In some embodiments, a structure may be produced with skives already formed, with no need for further material removal. The skive of the structure refers to the slot, cut, or other opening in the structure. With respect to a catheter shaft, as discussed herein, a skive refers to a slot, cut, or other opening in a wall of a catheter shaft. In some embodiments, skives in a catheter penetrate the wall of the catheter shaft. In some embodiments, skives in a catheter result from the removal of catheter shaft wall material without penetrating the wall entirely. The skive 130 may extend through the middle wall portion 111 to expose the guidewire lumen 114 of the distal shaft 108. In some embodiments, the skive(s) 130 may reduce the cross-sectional area/profile uniformly over the length of the skive. In some embodiments, the skive(s) 130 may provide a varying cross-sectional profile over the length of the skive(s) 130.

In some embodiments, the catheter 100 includes a stiffening wire 105. The stiffening wire 105 may be provided to insure increased strength and pushability of the catheter 100 through the middle wall portion 111 having the skive 130. The stiffening wire 105 is an optional feature that may or may not be included in each of the embodiments described herein, and is discussed in greater detail below with respect to FIGS. 9-11.

FIGS. 2A-2H illustrate some examples of skives in a tubular shaft 201. The tubular shaft 201 in each of FIGS. 2A-2H may be the distal shaft 108 of FIG. 1. In particular, the tubular shaft 201 includes a wall 211 which may be the middle wall portion 111 of the distal shaft 108 of FIG. 1.

FIGS. 2A and 2B illustrate a single penetrating slot skive 202. FIG. 2A is a perspective view of the tubular shaft 201 having a penetrating slot skive 202, which reduces the cross-sectional profile of the tubular shaft 201. By "penetrating", it is meant that the skive extends through the entire cross-sectional thickness of the wall 211 through to a lumen 214 of the tubular shaft 201. FIG. 2B illustrates a cross-section of the tubular shaft 201 at a location of the slot skive 202. The slot skive 202 penetrates the entire depth of the wall 211 of the tubular shaft 201, exposing the lumen 214, and, as illustrated, has a rectangular shape. Further, the slot skive 202 extends longitudinally along the wall portion 211. In some embodiments, the slot skive may be parallel to a central longitudinal axis 250 of the tubular shaft 201. In some embodiments, the slot skive 202 may be of different shapes, including ellipses, squares, rectangles with rounded corners, and any other suitable shape.

FIGS. 2C and 2D illustrate a pair of penetrating slot skives 202. FIG. 2C is a perspective view of the tubular shaft 201 having a pair of penetrating slot skives 202, which reduce the cross-sectional profile of the tubular shaft 201. FIG. 2D illustrates a cross-section of the tubular shaft 201 at a location of the slot skives 202. The slot skives 202 penetrate the entire depth of the wall 211 of the tubular shaft 201, exposing the lumen 214, and, as illustrated, have a rectangular shape. In some embodiments, the slot skives 202 may be of different shapes, including ellipses, squares, rectangles with rounded corners, and any other suitable shape. Further, in some embodiments, the slot skives 202 may be parallel to a central longitudinal axis 250 of the tubular shaft 201. In other embodiments, the slot skives may be angled (non-zero angle) with respect to the central longitudinal axis 250.

FIGS. 2E and 2F illustrate a skive 204 removing a significant portion of the circumference of the wall 211 of the tubular shaft 201. FIG. 2E is a perspective view of the tubular shaft 201 and FIG. 2F is a cross-section view. As can be seen in FIG. 2F, the skive 204 reduces the cross-sectional profile of the tubular shaft 201. In some embodiments, the skive 204 extends around a majority of the circumference of the tubular shaft 201, while in other embodiments, the skive 204 extends around only a minority of the circumference of the tubular structure 201. As shown in FIG. 2E, the skive 204 may have a varying depth along its length relative to the diameter of the tubular shaft 201. Thus, in the embodiment shown, at the center of the length of the skive 204, the skive 204 is at its greatest depth, while at either end, the skive 204 becomes shallow. Although the skive 204 is illustrated with an arc shape, similar skives of varying depth may have linear shapes, e.g., trapezoidal and/or pyramidal.

FIGS. 2G and 2H illustrate a pair of non-penetrating skives 205 in the wall of the tubular shaft 201. FIG. 2G is a perspective view of the tubular shaft 201 and FIG. 2H is a cross-section view. As can be seen in FIG. 2H, the skive 205 reduces the cross-sectional profile of the tubular structure 201. The skive 205 does not fully penetrate the wall 211 of the tubular shaft 201 and therefore does not expose the lumen 214. As illustrated in FIGS. 2G and 2H, the tubular shaft may have two non-penetrating skives 205. In some embodiments, more or fewer non-penetrating skives 205 may be included. In some embodiments, an entire circumference of the tubular structure 201 may be skived with a single circumferential skive 205 that reduces the cross-sectional profile uniformly around the tubular shaft 201. In the embodiment shown, the two skives 205 extend longitudinally substantially parallel to the central longitudinal axis 250 of the tubular shaft 201. In other embodiments, the skives 205 may extend at an angle (non-zero angle) relative to the central longitudinal axis 250.

Figure 3A:
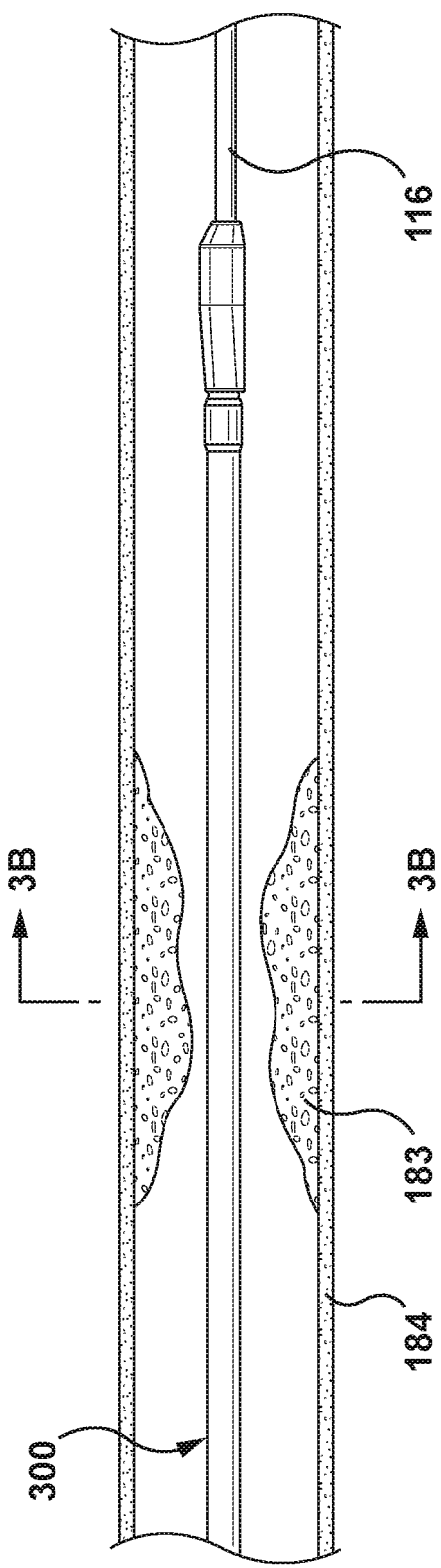
FIGS. 3A-3D illustrate close up views of a skived catheter and an un-skived catheter in a vessel with a stenosis, consistent with embodiments described herein.
Figure 3B:
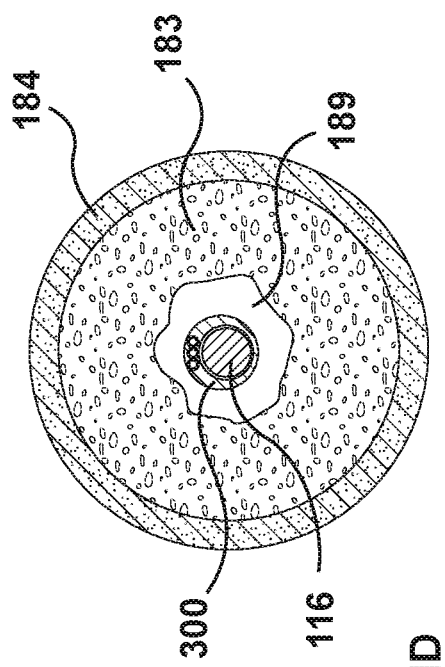
Figure 3C:
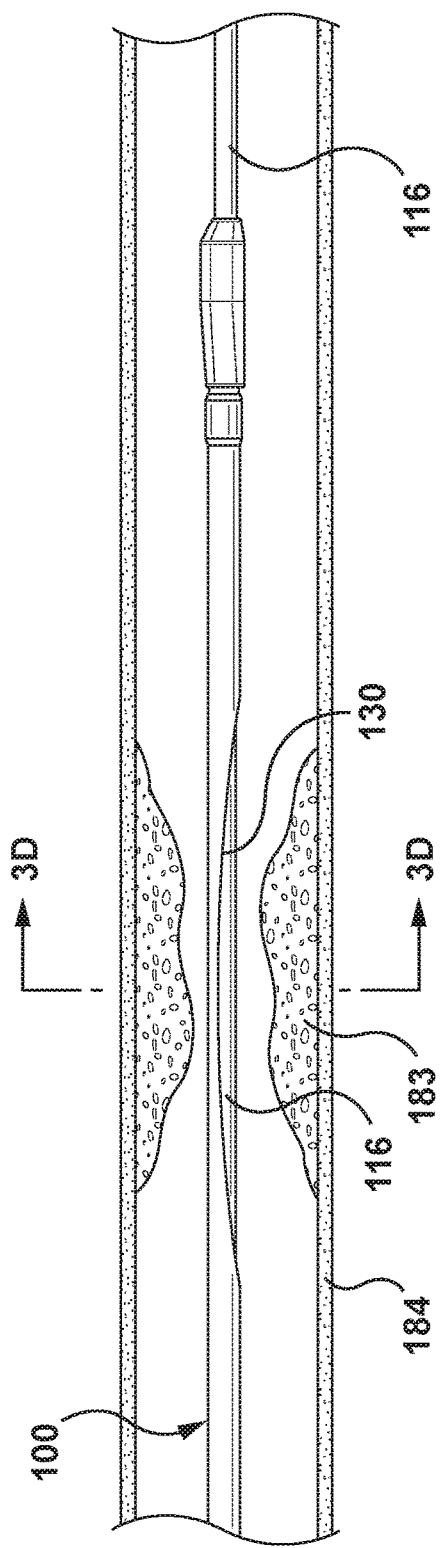
Figure 3D:
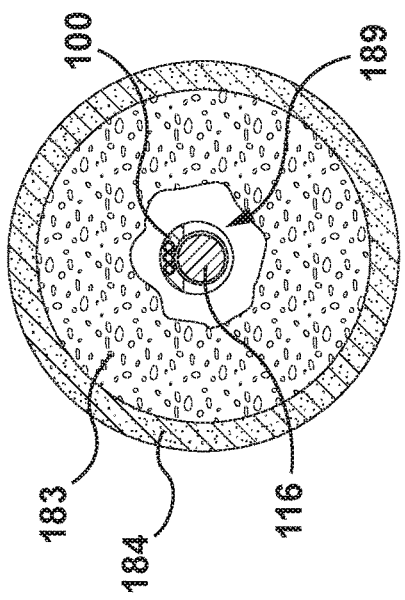

As explained above, the catheter 100 having the skive(s) 130 reduces the occupied or blocked cross-sectional area across the stenosis 183 as compared to a standard FFR catheter having no skives. FIGS. 3A-3D illustrate a comparison between a standard FFR catheter 300 (or microcatheter) and the catheter 100 having the skive 130. FIGS. 3A and 3C respectively illustrate plan views of the standard FFR catheter 300 and the skived catheter 100 extending through the intra-stenosis lumen 189 of the stenosis 183. FIGS. 3B and 3D respectively illustrate cross-sectional views of the standard FFR catheter 300 and the skived catheter 100 extending through the intra-stenosis lumen 189 of the stenosis 183. As shown in FIG. 3A, the standard catheter 300 (or microcatheter) extending through the stenosis 183 blocks a significant portion of the intra-stenosis lumen 189, leaving less room for blood to flow. In contrast, as shown in FIG. 3B, with the catheter 100 in place, having the skive 130 at the location of the stenosis 183, the free and unblocked portion of the intra-stenosis lumen 189 is larger, enabling more room for blood to flow. A blockage of flow through the stenosis 183 may serve to artificially reduce the measured pressure $P_d$ at the distal portion 185 of the blood vessel 184, which, in turn, reduces the FFR measurement. A larger blockage may result in a larger deviation of FFR measured using a catheter as compared to FFR measured using an FFR wire. Thus, reducing the cross-sectional profile of the catheter 100 using the skive 130 leads to a smaller potential for error in the distal pressure $P_d$, and hence a smaller potential for error in the FFR calculation. In some implementations, the blockage of the intra-stenosis lumen 189 may be further reduced by the retraction of the guidewire 116 prior to measuring the distal pressure $P_d$.

FIGS. 4-8 illustrate alternative skives consistent with embodiments of the present invention. One or more of the skives illustrated in FIGS. 4-8 may be implemented to reduce a cross-sectional profile of the catheter 100 in a portion designed to extend across the stenosis 183. Additional skives that are not pictured may be implemented without departing from the scope of this disclosure.

FIGS. 4A-4D illustrate a catheter 400 having dual opposing skives 430 in a middle wall portion 411 of a distal shaft 408. Catheter 400 is an FFR catheter that may include all of the features previously described with respect to catheter 100. Catheter 400 differs from catheter 100 in the shape of the skives 430 in the middle wall portion 411. FIG. 4A illustrates a side view, FIG. 4B a plan view, FIG. 4C a perspective view, and FIG. 4D a cross-sectional view. Dual opposing skives 430 extend through the middle wall portion 411 of the distal shaft 408, exposing a guidewire lumen 414 and a guidewire 416, if present. In the embodiment shown, the dual opposing skives 430 are equally spaced about a circumference of the middle wall portion 411 of the distal shaft 430. In other words, the dual opposing skives 430 are disposed symmetrically about the circumference of the middle wall portion 411. In such an embodiment, the symmetric nature of the resultant middle wall portion 411 may contribute to the stability of the catheter and reduce the potential for kinking and/or bending in the skived portion. The remaining symmetric portions of the middle wall portion 411 may provide increased columnar strength. Also illustrated in FIG. 4C are the pressure wires 420, which extend to a pressure sensor (not shown) located at the distal wall portion of the distal shaft 408. FIG. 4D illustrates a cross-sectional view of the catheter 400 extending through the intra-stenosis lumen 189 of the stenosis 183 of the blood vessel 184. Although illustrated in the middle wall portion 411, the skives 430 may extend past the middle wall portion 411 either proximally or distally.

FIGS. 5A and 5B illustrate the catheter 400 having dual opposing skives 430 in the middle wall portion 411 of the distal shaft 408, with the guidewire 416 (not illustrated in FIGS. 5A and 5B) retracted for FFR measurement. During an FFR procedure, the guidewire 416 over which the catheter 400 has been advanced may be retracted proximal of the dual opposing skives 430 prior to measuring the distal pressure $P_d$. As shown in FIGS. 5A and 5B, retraction of the guidewire 416 may further increase an unobstructed flow area through the intra-stenosis lumen 189. As discussed above and illustrated in the cross-sectional view of FIG. 5B as compared to that of FIG. 4D, the retraction of the guidewire 416 may serve to further reduce the cross-sectional area occupied by components of the FFR catheter system. Within the intra-stenosis lumen 189, blood may flow through the skives 430 and into the unoccupied guidewire lumen 414, thereby enabling the blood to flow within the guidewire lumen 414 of the distal shaft 408. The increase in the unblocked portion of the intra-stenosis lumen 189 by the reduced middle wall portion cross-sectional profile and by blood flowing through the guidewire lumen 414 may result in a measured distal pressure $P_d$ that is more closely aligned with a distal pressure measurement taken with an FFR guidewire. This may alleviate any need for a correction factor to be applied to the FFR calculated from pressure measurements using an FFR catheter. Although not specifically discussed with respect to every embodiment described herein, guidewire retraction may serve to increase the unblocked portion of the intra-stenosis lumen 189 in many embodiments including skives penetrating through the walls of a catheter shaft to a guidewire lumen or other lumen.

FIGS. 6A-6C illustrate a catheter 600 having multiple skives 630 disposed around the circumference of a middle wall portion 611 of a distal shaft 608. The catheter 600 is an FFR catheter that may include all of the features previously described with respect to catheter 100. The catheter 600 differs from the catheter 100 in the shape of the skives 630 in the middle wall portion 611. FIG. 6A illustrates a side view of the catheter 600, FIG. 6B a perspective view of the catheter 600, and FIG. 6C a cross-sectional view of the catheter 600 extending through the intra-stenosis lumen 189 of the stenosis 183 of the blood vessel 184. The multiple skives 630 may include any number of skives penetrating the middle wall portion 611 to expose a guidewire lumen 614 and a guidewire 616 (if present). The multiple skives 630 may permit the removal of more material from the middle wall portion 611 while maintaining an enclosure for the guidewire 616 such that the catheter 600 may be tracked over the guidewire 616. The skives 630 may permit embodiments in which the guidewire 616 is retracted to further decrease a cross-sectional area of the catheter system extending through the intra-stenosis lumen and to enable blood flow through the guidewire lumen 614 during FFR measurements. Also illustrated in FIG. 6B are pressure wires 620, which extend to a pressure sensor (not shown) located at the distal wall portion of the distal shaft 608. Although illustrated in the middle wall portion 611, the skives 630 may extend past the middle wall portion 611 either proximally or distally. In the embodiment shown in FIGS. 6A-6C, each of the skives 630 extends longitudinally and is substantially parallel to a central longitudinal axis 650 of the distal shaft 608. Also in the embodiment shown in FIGS. 6-A-6C, the skives 630 are equally spaced around the circumference of the middle wall portion 611 except in the area of the sensor wires 620, where there are no skives. Other shapes and distributions of the skives 630 may be utilized in keeping with the purposes described herein.

Figure 7:
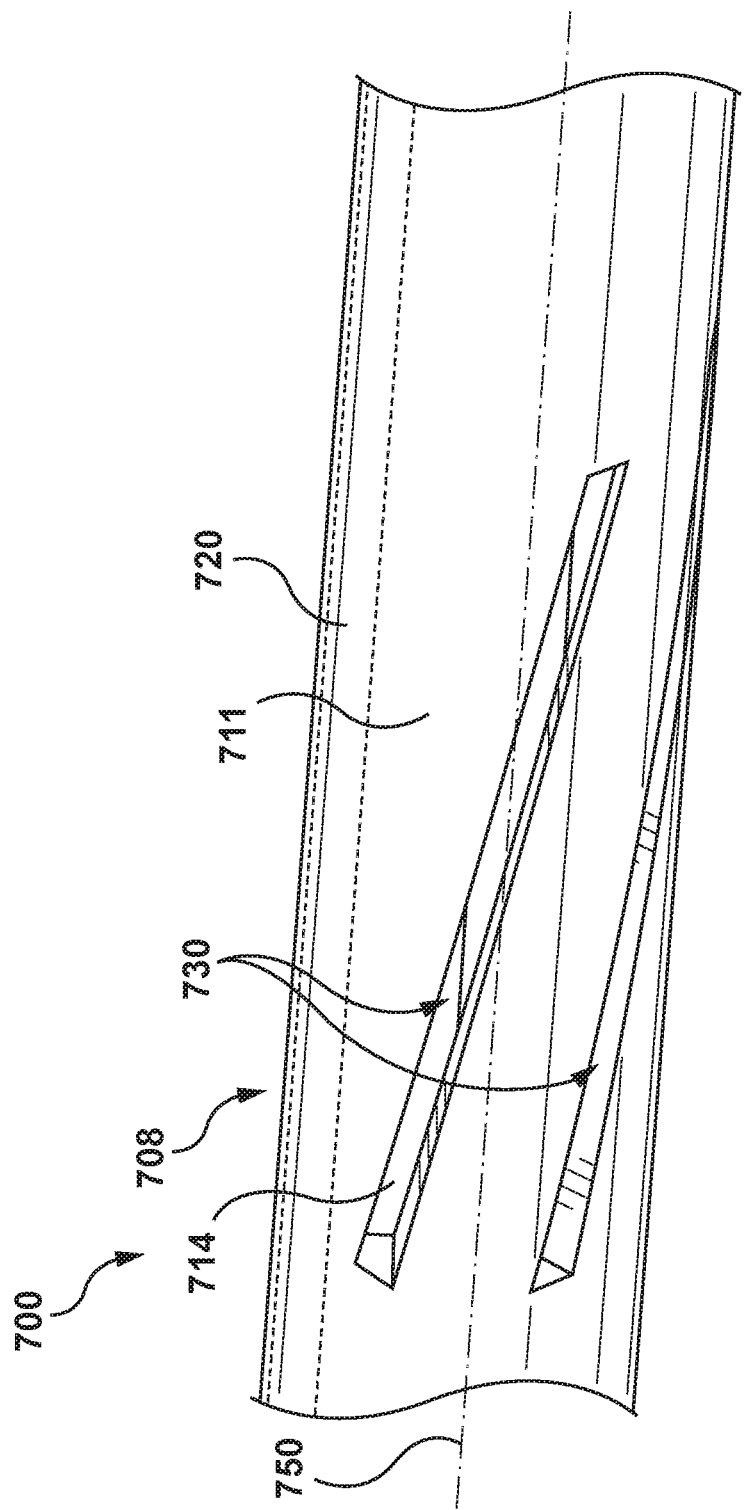
FIG. 7 illustrates a catheter having multiple angled skives, consistent with embodiments described herein.

FIG. 7 illustrates a catheter 700 having multiple angled skives 730 disposed around the circumference of a middle wall portion 711 of a distal shaft 708. The catheter 700 is an FFR catheter that may include all of the features previously described with respect to catheter 100. The catheter 700 differs from the catheter 100 in the shape of the skives 730 in the middle wall portion 711. The multiple angled skives 730 may include any number of skives 730 penetrating the middle wall portion 711 to expose a guidewire lumen 714 and a guidewire (not illustrated). The angled skives 730 may be arranged at any non-zero angle with respect to a longitudinal axis 750 of the distal shaft 708. The multiple angled skives 730 may be arranged at multiple different angles, or they may each be disposed at the same non-zero angle with respect to the central longitudinal axis 750. The multiple angled skives 730 are configured to increase columnar strength of the distal shaft 708 and thus maintain pushability of the catheter. The multiple angled skives 730 may permit embodiments in which a guidewire is retracted to further decrease a cross-sectional area of the catheter system extending through the intra-stenosis lumen and to enable blood flow through the guidewire lumen during FFR measurements. Also illustrated in FIG. 7 are the pressure wires 720, which extend to a pressure sensor (not shown) located at the distal wall portion of the distal shaft 708. Although illustrated in the middle wall portion 711, the skives 730 may extend past the middle wall portion 711 either proximally or distally. The skives 730 may be equally spaced around the circumference of the middle wall portion 711, or may be equally spaced around the circumference except in the area of the sensor wires 720, where there are no skives. Other shapes and distributions of the skives 730 may be utilized in keeping with the purposes described herein.

FIGS. 8A-8C illustrate a catheter 800 having a pair of non-penetrating skives 830 in a middle wall portion 811 of a distal shaft 808. Catheter 800 is an FFR catheter that may include all of the features previously described with respect to the catheter 100. The catheter 800 differs from the catheter 100 in the shape of the skives 830 in the middle wall portion 811. FIG. 8A is a cross-sectional perspective view, FIG. 8B is a perspective view, and FIG. 8C is a cross-sectional view of the catheter 800 extending through the intra-stenosis lumen 189 of the stenosis 183 of the blood vessel 184. Also illustrated in FIGS. 8A and 8B are the pressure wires 820, which extend to a pressure sensor (not shown) located at the distal wall portion of the distal shaft 808 and a guidewire 816. The non-penetrating skives 830 may reduce the profile and cross-sectional area of the middle wall portion 811, but do not penetrate the catheter shaft wall to expose the guidewire lumen 814 to blood flow. The non-penetrating skives 830 may take any shape, form, or number that reduces the cross-sectional area of the distal shaft 808 at the middle wall portion 811. Although illustrated in the middle wall portion 811, the skives 830 may extend past the middle wall portion 811 either proximally or distally.

Figure 10A:
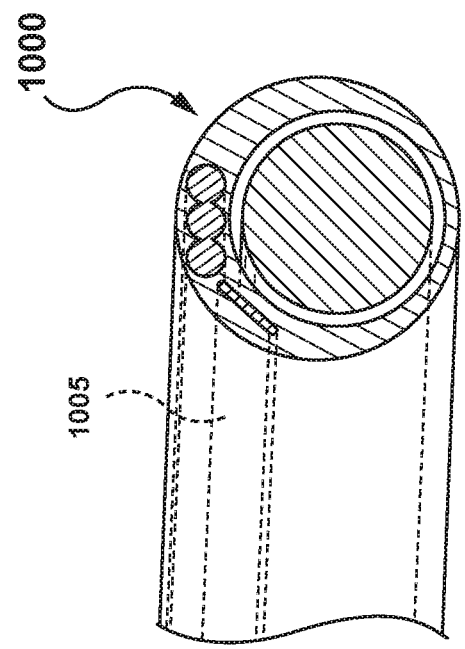
FIGS. 10A-10B illustrate a catheter having a flat stiffening wire, consistent with embodiments described herein.
Figure 10B:
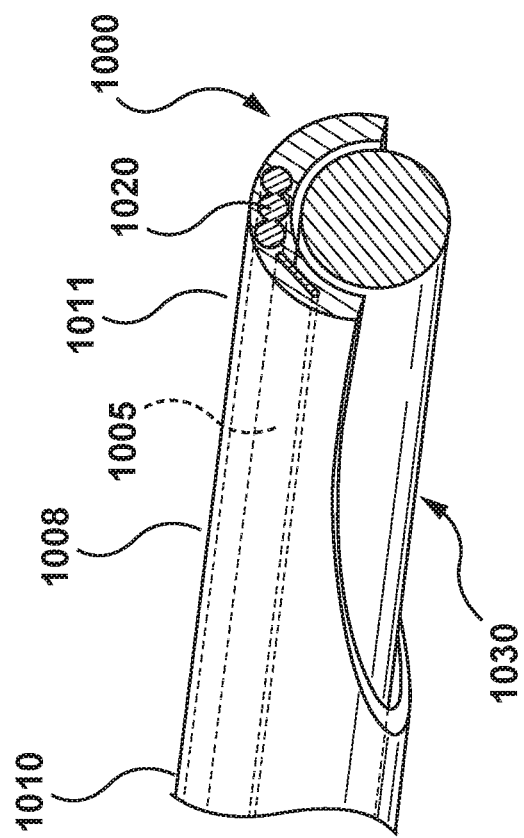
Figure 11:
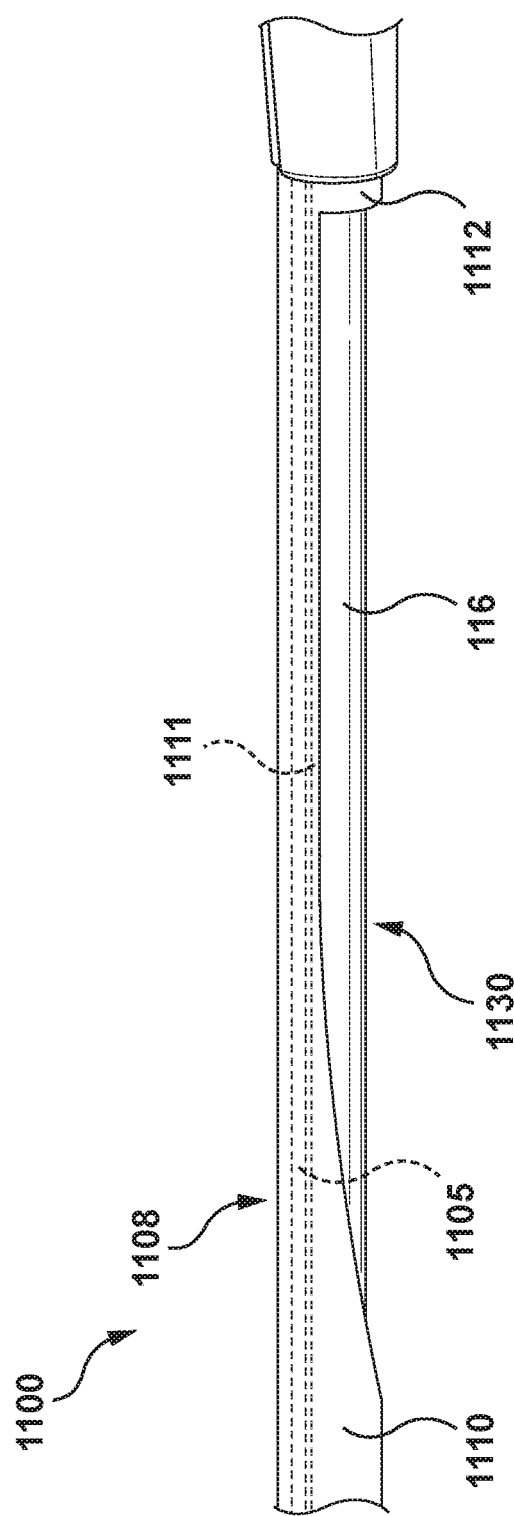
FIG. 11 illustrates a catheter including a stiffening wire extending from an unskived region through a skived region, consistent with embodiments described herein.

FIGS. 9-11 illustrate embodiments of a catheter having a skive and at least one stiffening wire. The catheters of FIGS. 9-11 are FFR catheters that may include all of the features previously described with respect to catheter 100. Furthermore, these catheters may include skives consistent with those of any of the previously discussed embodiments. A catheter including a skive to reduce the cross-sectional area may also have reduced columnar strength or pushability through the skived portion, due to the reduced amount of material. To counteract this effect, the skived portion of the catheter, as well as other portions, may include one or more stiffening wires embedded in the shaft wall. In some embodiments, the stiffening wires may extend through a length of the catheter, e.g., through the proximal shaft and the distal shaft. Stiffening wires may include wires having a round, flat, curved, or any other suitable shape. Although illustrated in FIGS. 9-11 as single stiffening wires, multiple stiffening wires may be included in alternative embodiments. Stiffening wires may be constructed of any appropriate material, including metals, plastics, polymers, and other materials.

FIGS. 9A-9B respectively illustrate a perspective view and a cross-section of a middle wall portion 911 of a distal shaft 908 of a catheter 900. The catheter 900 is an FFR catheter that may include all of the features previously described with respect to the catheter 100. The catheter 900 further includes a stiffening wire 905. Although not illustrated in FIGS. 9A-9B, the catheter 900 may include a skive that may be similar to the skive 130 in FIG. 1 and the skive 204 of FIGS. 2E-2F. However, the catheter 900 is not limited to this skive design. The catheter 900 may include any cross-sectional area reducing skive consistent with embodiments described throughout this disclosure. In some embodiments, catheter 900 may include no skived portion. Also illustrated are sensor wires 920 which may extend to a pressure sensor (not shown) at a distal end of the catheter 900. The circular stiffening wire 905 may be disposed within a wall portion of the distal shaft 908 of the catheter 900. The circular stiffening wire 905 is disposed longitudinally throughout the middle wall portion 911, and may, in some embodiments, further extend into a distal wall portion and/or a proximal wall portion of the distal shaft 908. In some embodiments, the circular stiffening wire 905 may extend to a proximal shaft (not shown) of the catheter 900. The addition of the circular stiffening wire 905 may increase the columnar strength, pushability, and kink resistance of the catheter 900, particularly in the skived portion. This may assist in delivering the catheter 900 to a treatment site, as during delivery the catheter 900 typically experiences increased resistance due to the size of the vessels and the tortuous path taken through the vasculature to the treatment site. Further, the increased columnar strength, pushability, and kink resistance may assist in pushing the catheter 900 through the stenosis 183, which may hamper the forward movement of the catheter 900 (i.e., provide increased resistance to the catheter 900). In such cases, the circular stiffening wire 905 may serve to ensure that the catheter 900 does not bend, buckle, or otherwise fail during delivery across the stenosis 183.

FIGS. 10A and 10B illustrate a distal shaft 1008 of catheter 1000 including a flat stiffening wire 1005. FIG. 10A shows a middle wall portions 1011 of the distal shaft 1008 and FIG. 10B shows a proximal wall portion 1010 of the distal shaft 1008. The catheter 1000 is an FFR catheter that may include all of the features previously described with respect to the catheter 100. The catheter 1000 further includes a flat stiffening wire 1005. As illustrated in FIG. 10A, the catheter 1000 includes a skive 1030 that is similar to the skive 130 of FIG. 1 and the skive 204 of FIGS. 2E-2F, but the catheter 1000 is not limited to this skive design. The catheter 1000 may include any cross-sectional area reducing skive consistent with embodiments described throughout the disclosure. Also illustrated are sensor wires 1020 which may extend to a pressure sensor (not shown) at a distal end of the catheter 1000. The flat stiffening wire 1005 may be disposed within a wall portion of the distal shaft 1008 of the catheter 1000. The flat stiffening wire 1005 is disposed longitudinally throughout the middle wall portion 1011. In the embodiment shown in FIG. 10B, the flat stiffening wire 1005 extends proximally at least into the proximal wall portion 1010 of the distal shaft 1008. In some embodiments, the flat stiffening wire 1005 may extend distally into a distal wall portion of the distal shaft 1008, and/or to a proximal shaft of the catheter 1000. The addition of the flat stiffening wire 1005 may increase the columnar strength, pushability, and kink resistance of the catheter 1000 in the skived portion. This may assist in delivering the catheter 900 to a treatment site, as during delivery the catheter 1000 typically experiences increased resistance due to the size of the vessels and the tortuous path taken through the vasculature to the treatment site. Further, the increased columnar strength, pushability, and kink resistance may assist in pushing the catheter 900 through the stenosis 183, which may hamper the forward movement of the catheter 1000 (i.e., provide increased resistance to the catheter 1000). In such cases, the flat stiffening wire 1005 may serve to ensure that the catheter 1000 does not bend, buckle, or otherwise fail during delivery across the stenosis 183.

FIG. 11 illustrates a catheter 1100 including a stiffening wire 1105 extending beyond a middle wall portion 1111 of a distal shaft 1108 into a distal wall portion 1112 and a proximal wall portion 1110 of the distal shaft 1108. The catheter 1100 is an FFR catheter that may include all of the features previously described with respect to catheter 100. As illustrated in FIG. 11, the catheter 1100 includes a skive 1130 that eliminates a section of the catheter wall, but the catheter 1100 is not limited to this skive design. The catheter 1100 may include any cross-sectional area reducing skive consistent with embodiments described through the disclosure. Also illustrated is a guidewire 1116 extending through a guidewire lumen of the distal shaft 1108. The catheter 1100 may also include sensor wires (not shown) which may extend to a pressure sensor (not shown) at a distal end of the catheter 1100. Extending the stiffening wire 1105 past the middle wall portion 1110 on either end may increase the columnar strength, pushability, and kink resistance of catheter 1100 in the skived portion. In some embodiments, the stiffening wire 1105 may be extended to a proximal shaft of the catheter 1100. The increased columnar strength, pushability, and kink resistance may assist in delivering the catheter 1100 to a treatment site, as during delivery the catheter 1100 typically experiences increased resistance due to the size of the vessels and the tortuous path taken through the vasculature to the treatment site. Further, the increased columnar strength, pushability, and kink resistance may assist in pushing the catheter 900 through the stenosis 183, which may hamper the forward movement of the catheter 1100 (i.e., provide increased resistance to the catheter 1100). In such cases, the stiffening wire 1105 may serve to ensure that the catheter 1100 does not bend, buckle, or otherwise fail during delivery across the stenosis 183.

Figure 12:
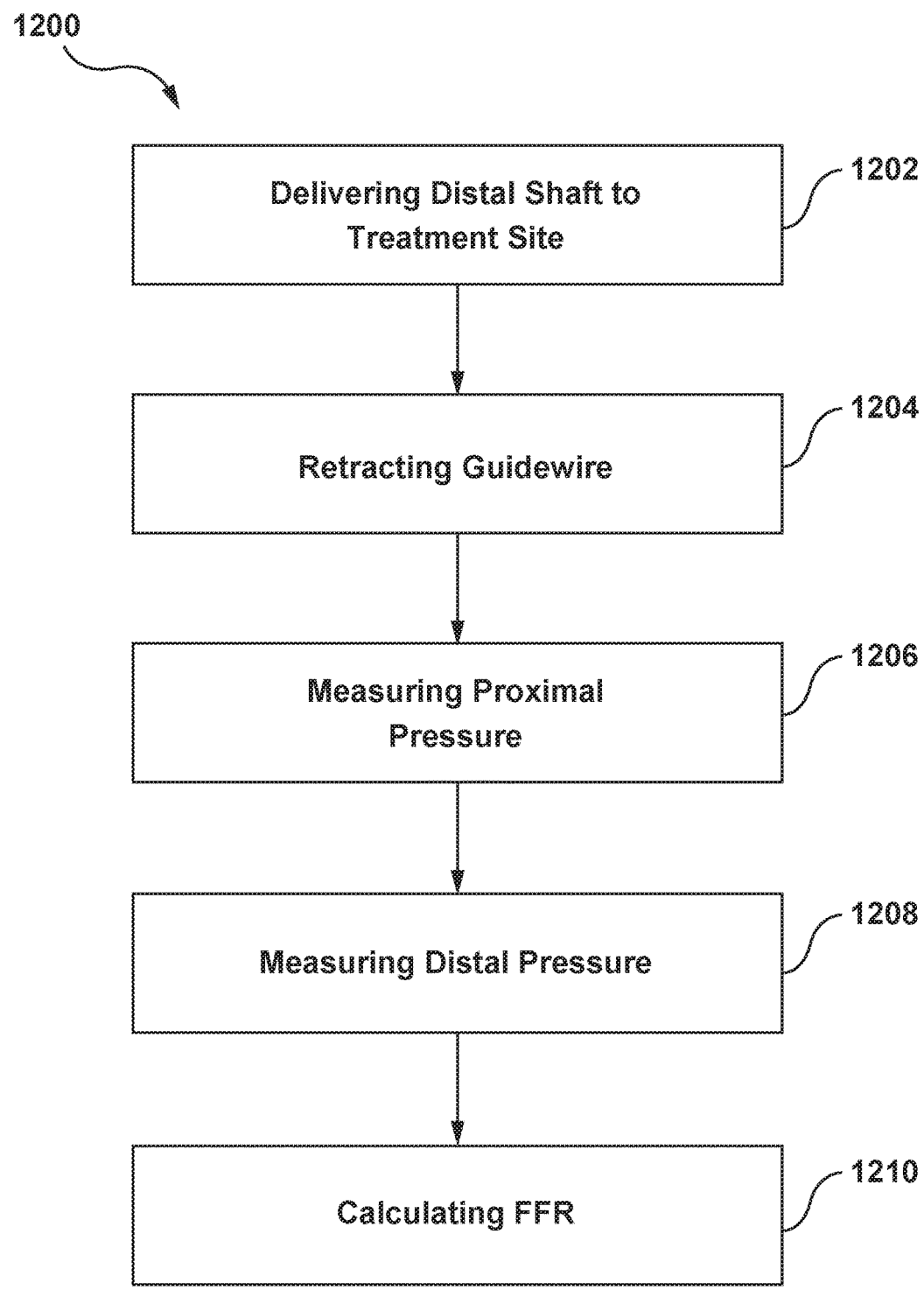
FIG. 12 is a flowchart illustrating a method of determining FFR.

FIG. 12 is a flowchart of an FFR calculation method 1200, suitable for performance with catheters described herein. The method 1200 will be described using the catheter 100. However, this is not meant to be limiting, and the method 1200 may be used with any of the skived FFR catheters described above, and variations thereof.

In an operation 1202, the FFR catheter 100 is delivered to a treatment site in a vessel of a patient. In an example, referring again to FIG. 1, the guide catheter 180 and the guidewire 116 may be advanced through the vasculature to a desired treatment site. For example, and not by way of limitation, if the vessel 184 is a coronary artery, the guidewire 116 may be advanced through the aorta, into the coronary artery, and through the stenosis 183. The guide catheter 180 may be advance to the ostium of the coronary artery. The guidewire 116 may be back-loaded into the catheter 100 (i.e., the proximal end of the guidewire 116 is loaded into the distal end of the guidewire lumen 114 at the distal guidewire port 113 of the distal shaft 108). The catheter 100 may then be advanced over the guidewire 116 and through the lumen 188 of the guide catheter 180 to the desired treatment site. With a distal end of the guide catheter 180 disposed at the desired site proximal of the stenosis 183, such as in the sinus of an aortic valve, the distal shaft 108 of the catheter 100 is advanced through the lumen 188 distally of the distal end of the guide catheter 180. The catheter 100 is advanced such that distal shaft 108 is disposed across the stenosis 183 of the vessel 184. The catheter 100 is delivered to the treatment site such that distal wall portion 112 is disposed on a distal side 185 of a stenosis 183 of the vessel 184, the skive 130 of middle wall portion 111 is disposed through an intra-stenosis lumen 189 of the stenosis 183, and the proximal wall portion 110 is disposed on a proximal side 182 of the stenosis 183 of the vessel 184.

In an operation 1204, the guidewire 116 is retracted from the distal shaft 108 proximal to the intra-stenosis lumen 189. The guidewire 116 is preferably not fully removed from the guidewire lumen 114 of the distal shaft 108. When the guidewire 116 is retracted, blood may flow through skive 130, into and through the guidewire lumen 114 of the distal shaft 108. This permits reduced blockage of the intra-stenosis lumen 189 because the effective cross-sectional profile of the catheter 100 through the intra-stenosis lumen 189 is the thickness of the walls of the middle wall portion 111. This reduced cross-sectional profile through the intra-stenosis lumen 189 enables the measured distal pressure $P_d$ using pressure sensor 118 to closely match the measured distal pressure using an FFR wire. Thus, a correction factor may not be needed. Retraction of the guidewire 116 prior to pressure measurements may be performed to facilitate an increase in the area of unblocked intra-stenosis lumen 189. In some embodiments, the guidewire 116 may remain in place while pressure measurements are performed, such as, for example, embodiments where the skive(s) do not penetrate to the guidewire lumen 116.

In an operation 1206, the proximal pressure $P_a$ is measured. As discussed above, the proximal pressure $P_a$ may be measured via the external pressure transducer 186. In other embodiments (not shown), the proximal pressure $P_a$ may be measured using pressure sensors/transducers located on the catheter. In other embodiments, the proximal pressure $P_a$ may be measured using the pressure sensor 118 located on the distal shaft 108 by moving the catheter 100 such that the pressure sensor 118 is located on the proximal side 182 of the stenosis 183. Any suitable method may be used to measure the proximal pressure $P_a$, and the scope of the invention is not limited by methods described herein. The measured proximal pressure $P_a$ is communicated to the processor 140 via the pressure transducer wire 191, as explained above. However, as also explained above, this is not meant to limit the design and the measured proximal pressure $P_a$ may be communicated to the processor 140 by any means suitable for the purposes described herein.

In an operation 1208, the distal pressure $P_d$ is measured via the pressure sensor 118. The pressure sensor 118 is coupled to the processor 140 via sensor wires 120 and/or by other coupling means, such as wireless means, as described above.

The pressure measuring operations 1206 and 1208 may be performed substantially simultaneously in some embodiments. In some embodiments, the pressure measuring operations 1206 and 1208 may be performed close in time to another, e.g., one after another. In some embodiments, the pressure measuring operations 1206 and 1208 may be performed continuously for a period of time, thus permitting an on-going measurement of a patient's FFR over a set period of time.

In an operation 1210, the FFR is computed according to the measured proximal pressure $P_a$ and the measured distal pressure $P_d$. FFR is computed as the ratio of the measured distal pressure $P_d$ to the measured proximal pressure $P_a$ ($FFR=P_d/P_a$). FFR may be calculated by the processor 140 or other means suitable for the purposes described herein.

Presented herein are various embodiments of an FFR catheter including a skived portion having a reduced cross section of a distal shaft. Various implementations of a catheter skive are presented. Also presented are various implementations of a stiffening wire running through a wall portion of the distal shaft to improve catheter strength in and near the skived portion. It is understood that the scope of the present disclosure includes any of the embodiments and implementations of the skives utilized with any of the embodiments and implementations of the stiffening wires. Furthermore, combinations of multiple types of stiffening wires and/or multiple types of skives are also consistent with the scope of the present disclosure. Use of the skived FFR catheters as described herein may enable the measurement of an FFR more closely reflective of FFR as measured by a standard 0.014" FFR guidewire than an FFR measured using an unskived catheter.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. For example, and not by way of limitation, the embodiments describing a radially expandable/collapsible proximal shaft may be combined with the embodiments describing a radially expandable/collapsible distal shaft. All patents and publications discussed herein are incorporated by reference herein in their entirety.

What is claimed is:

1. A catheter for measuring a fractional flow reserve, the catheter comprising:
   a proximal shaft;
   a distal shaft defining a guidewire lumen configured to receive a guidewire therein and including a proximal wall portion, a middle wall portion, and a distal wall portion;
   a pressure sensor coupled to the distal wall portion of the distal shaft;
   a skive in the middle wall portion configured to reduce a cross sectional area of the middle wall portion, extending longitudinally along an entire length of the middle wall portion configured to extend across an intra-stenosis lumen of a stenosis of a patient vessel, configured to extend around a majority of a circumference of the distal shaft in at least a portion of the middle wall portion, and extending radially through the middle wall portion exposing the guidewire lumen; and at least one stiffening wire embedded in a wall of the distal shaft at the middle wall portion and configured to increase columnar strength of the distal shaft at the middle wall portion.

2. The catheter of claim 1, wherein the stiffening wire extends past the middle wall portion into at least one of the proximal wall portion and the distal wall portion.

3. The catheter of claim 1, wherein the stiffening wire terminates at a proximal end and a distal end of the middle wall portion.

4. The catheter of claim 1, further comprising at least one pressure sensor wire extending through the proximal wall portion, the middle wall portion, and the distal wall portion, the at least one pressure sensor wire being coupled to the pressure sensor.

5. The catheter of claim 1, wherein the skive is further configured to reduce a portion of an intra-stenosis lumen blocked by the catheter when the middle wall portion is deployed across a vascular stenosis.

6. The catheter of claim 1, wherein the at least one stiffening wire is embedded in a same section of the middle wall portion as the skive is located.

7. The catheter of claim 1, wherein the skive extends a varying depth into the distal shaft relative to the diameter of the distal shaft along the length.

8. The catheter of claim 1, wherein the skive is configured to enable increased blood flow through the intra-stenosis lumen when the guidewire remains in place.

9. The catheter of claim 1, wherein the skive is configured to enable blood flow through the guidewire lumen when the guidewire is retracted.

10. A method for calculating a fractional flow reserve in a vessel using a catheter, the method comprising:

delivering a distal shaft of the catheter to a treatment site in the vessel via a guidewire, the distal shaft defining a guidewire lumen configured to accommodate the guidewire and having a distal wall portion, a middle wall portion, and a proximal wall portion, the middle wall portion having a skive reducing a cross sectional profile of the distal shaft at the middle wall portion, extending radially through the middle wall portion to expose the guidewire lumen, configured to extend around a majority of a circumference of the distal shaft in at least a portion of the middle wall portion, and extending longitudinally along an entire length of the middle wall portion configured to extend across an intra-stenosis lumen of a stenosis of a patient vessel, and at least one stiffening wire embedded with a wall of the distal shaft at the middle wall portion, the at least one stiffening wire configured to increase columnar strength of the distal shaft at the middle wall portion, the catheter including a pressure sensor coupled to the distal wall portion, wherein the distal shaft is delivered to the treatment site such that the distal wall portion is disposed on a distal side of a stenosis of the vessel, the skive of the middle wall portion is disposed through an intra-stenosis lumen of the stenosis, and the proximal wall portion is disposed on a proximal side of the stenosis of the vessel, measuring the distal pressure distal of the stenosis using the pressure sensor;

measuring a proximal pressure proximal of the stenosis; and calculating the fractional flow reserve using the measured distal pressure and the measured proximal pressure.

11. The method of claim 10, wherein the stiffening wire extends past the middle wall portion into at least one of the proximal wall portion and the distal wall portion.

12. The method of claim 10, wherein the stiffening wire terminates at a proximal end and a distal end of the middle wall portion.

13. The method of claim 10, wherein the catheter further comprises at least one pressure sensor wire extending through the proximal wall portion, the middle wall portion, and the distal wall portion, the at least one pressure sensor wire being coupled to the pressure sensor.

14. The method of claim 10, wherein the middle wall portion having the skive disposed through the intra-stenosis lumen reduces a portion of the intra-stenosis lumen blocked by the catheter with respect to the distal wall portion being disposed through the intra-stenosis lumen.

15. The method of claim 10, wherein the at least one stiffening wire is embedded in a same section of the middle wall portion as the skive is located.

16. The method of claim 10, wherein the skive extends a varying depth into the distal shaft relative to the diameter of the distal shaft along the length.

17. The method of claim 10, further comprising retracting the guidewire to permit blood flow through the exposed guidewire lumen prior to measuring a distal pressure.

18. The method of claim 10, wherein measuring the distal pressure and measuring the proximal pressure are performed with the guidewire remaining in the guidewire lumen of the middle wall portion.

\* \* \* \* \*